United States Patent
Wang et al.

(10) Patent No.: US 10,028,658 B2
(45) Date of Patent: Jul. 24, 2018

(54) IMAGER FOR MEDICAL DEVICE

(71) Applicant: Welch Allyn, Inc., Skaneateles Falls, NY (US)

(72) Inventors: Ynjiun Paul Wang, Cupertino, CA (US); Chee Keen Lai, Singapore (SG); Jeffrey H. Schmidt, Manlius, NY (US)

(73) Assignee: WELCH ALLYN, INC., Skaneateles Falls, NY (US)

( * ) Notice: Subject to any disclaimer, the term of this patent is extended or adjusted under 35 U.S.C. 154(b) by 431 days.

(21) Appl. No.: 14/143,448

(22) Filed: Dec. 30, 2013

(65) Prior Publication Data
US 2015/0182114 A1    Jul. 2, 2015

(51) Int. Cl.
*A61B 5/00*     (2006.01)
*G06K 9/00*     (2006.01)
*H04M 1/02*     (2006.01)
*A61B 90/96*    (2016.01)
*A61B 90/90*    (2016.01)
*A61B 5/01*     (2006.01)
*G06K 9/32*     (2006.01)

(52) U.S. Cl.
CPC ............. *A61B 5/0008* (2013.01); *A61B 5/742* (2013.01); *A61B 90/90* (2016.02); *A61B 90/96* (2016.02); *A61B 5/01* (2013.01); *G06K 9/3258* (2013.01); *H04M 2250/52* (2013.01)

(58) Field of Classification Search
CPC .................................... G06K 9/325–9/3258
USPC ........................................................ 600/300
See application file for complete search history.

(56) References Cited

U.S. PATENT DOCUMENTS

| 4,121,574 A    | 10/1978 | Lester |
| 6,909,793 B1 * | 6/2005  | Mori ............ A61B 5/02055 348/14.07 |
| 7,967,190 B2   | 6/2011  | Hussey |
| 8,243,940 B2   | 8/2012  | Smith |
| 8,442,607 B2   | 5/2013  | Banet |

(Continued)

FOREIGN PATENT DOCUMENTS

GB    2408103    5/2005

OTHER PUBLICATIONS

Julian C.P. Cheung, Fully Automated Thermometer Calibration System at the Standards and Calibration Laboratory (SCL), The Government of the Hong Kong Special Administrative Region Standards and Calibration Laboratory (SCL), presented at Metrology in a Fast Paced Society Workshop & Symposium, NCSL International Workshop and Symposium, Jul. 17, 2013, 24 pages.

(Continued)

*Primary Examiner* — Michael C Stout
(74) *Attorney, Agent, or Firm* — Merchant & Gould, P.C.

(57) ABSTRACT

A system for transmitting a temperature of a patient to an electronic medical record associated with the patient includes a thermometer with a digital display that is configured to display a temperature value associated with the temperature signal and at least one error-checking value. The system also includes a handheld imaging device including a camera to capture an image of the digital display of the thermometer, a processor to extract the text in the image using optical character recognition, and perform an error-check on the temperature value using the at least one error-checking value in the image, and to transmit the patient's identification number and temperature to an electronic medical record system.

7 Claims, 7 Drawing Sheets

(56) References Cited

U.S. PATENT DOCUMENTS

| | | | |
|---|---|---|---|
| 2003/0034900 A1* | 2/2003 | Han | G01D 4/004 340/870.02 |
| 2003/0163287 A1* | 8/2003 | Vock | A43B 3/0005 702/187 |
| 2004/0034779 A1 | 2/2004 | Wood et al. | |
| 2005/0035877 A1* | 2/2005 | Kim | H04Q 9/00 340/870.02 |
| 2007/0080223 A1 | 4/2007 | Japuntich | |
| 2007/0174152 A1 | 7/2007 | Bjornberg | |
| 2007/0282208 A1 | 12/2007 | Jacobs | |
| 2008/0011847 A1 | 1/2008 | Silverbrook et al. | |
| 2008/0221396 A1 | 9/2008 | Garces | |
| 2008/0262376 A1* | 10/2008 | Price | A61B 5/0002 600/547 |
| 2009/0192813 A1* | 7/2009 | Gejdos | G06F 19/323 |
| 2009/0326410 A1* | 12/2009 | James | A61B 10/0012 600/551 |
| 2010/0182631 A1* | 7/2010 | King | G06F 17/243 358/1.15 |
| 2010/0204596 A1* | 8/2010 | Knutsson | A61B 5/02055 600/509 |
| 2011/0028799 A1 | 2/2011 | Banet | |
| 2011/0082711 A1 | 4/2011 | Poeze | |
| 2012/0179006 A1* | 7/2012 | Jansen | A61B 5/0537 600/301 |
| 2012/0226771 A1 | 9/2012 | Harrington et al. | |
| 2012/0298755 A1* | 11/2012 | Lu | G06K 7/12 235/468 |
| 2012/0323590 A1 | 12/2012 | Udani | |
| 2013/0116515 A1 | 5/2013 | Banet | |
| 2013/0173968 A1* | 7/2013 | McVey | G06F 11/1004 714/49 |
| 2013/0191513 A1 | 7/2013 | Kamen | |
| 2013/0197320 A1 | 8/2013 | Albert et al. | |
| 2013/0207812 A1* | 8/2013 | Heydlauf | G01N 35/00871 340/691.6 |
| 2013/0234850 A1* | 9/2013 | Lee | A61B 5/02 340/539.12 |
| 2013/0267809 A1* | 10/2013 | Brister | A61B 5/14865 600/347 |
| 2013/0281801 A1 | 10/2013 | Proud | |
| 2014/0098209 A1* | 4/2014 | Neff | A61B 5/0033 348/77 |
| 2014/0155755 A1* | 6/2014 | Pinter | A61B 5/0008 600/474 |
| 2014/0237342 A1* | 8/2014 | King | G06F 17/30876 715/224 |
| 2014/0320677 A1* | 10/2014 | Jarvenpaa | H04N 5/23203 348/207.11 |
| 2015/0085155 A1* | 3/2015 | Diaz Spindola | G06T 19/006 348/222.1 |
| 2015/0145693 A1* | 5/2015 | Toriumi | A61B 5/746 340/870.17 |

OTHER PUBLICATIONS

International Search Report and Written Opinion in PCT/US2014/067344 dated Mar. 25, 2015, 20 pages.

\* cited by examiner

IMAGER FOR MEDICAL DEVICE

BACKGROUND

Many medical situations require taking the vital signs of a patient, such as the temperature of the patient. In some instances, the historical temperature trend of the patient must be monitored. Sometimes, the medical personnel taking the temperature are not the same as the medical personnel that diagnose the one or more conditions affecting the patient. Current thermometers do not provide an inexpensive and easy way to capture these temperature readings.

SUMMARY

In one aspect, a handheld imaging device is provided. The imaging device includes a housing, a camera supported by the housing and configured to capture an image containing text including both a value representing a physiological measurement and a checksum value, a processor operatively coupled to the camera, and configured to extract the text in the image using optical character recognition, and a network connection unit operatively coupled to the processor, where the network connection unit is configured to communicate with an electronic medical record system and to transmit at least some of the extracted text to the electronic medical record system.

Additionally, the handheld imaging device includes a processor configured to perform an error-control using the at least one checksum value in the image. The error-control can also include using an error detection function to verify an integrity of the value representing the physiological measurement, and an error correction function to correct any errors in the value representing the physiological measurement. The imaging device camera can be configured to image a temperature reading provided by a thermometer, a barcode, a quick response code, or a Microsoft® tag. The imaging device, whose housing can be a key fob, can communicate with the electronic medical system wirelessly.

Also provided is a system for transmitting a temperature of a patient to an electronic medical record associated with the patient. The system includes the handheld imaging device and a thermometer. The thermometer includes a housing, a temperature sensor, a digital display configured to display a temperature value associated with the temperature signal and at least one error-checking value. The digital display can be an e-ink display. The error checking value can be a checksum character. Also, the error checking can be performed using cyclic redundancy check-16 (CRC-16) or a Reed-Solomon error correction code.

Additionally, the electronic medical record system inputs the temperature value into the electronic medical record associated with the patient. The camera of the handheld imaging device can be further configured to capture a second image comprising a patient identifier. The patient identifier can be affixed to a patient wrist band or a patient bed.

Also provided is a method of sending a temperature of a patient to an electronic medical record associated with the patient. The method includes measuring the temperature of the patient using the thermometer, capturing an image of the display of the thermometer using a handheld image capture device, extracting text in the image using optical character recognition, checking the temperature in the extracted text using the error-checking value, and transmitting at least some of the extracted text to the electronic medical record system.

The method can also include scanning an identification code of the patient using the handheld image capture device and verifying an identity of the patient. Verifying the identity can include obtaining biometric data of the patient, such as an image of a face, an eye, or a fingerprint of the patient. The method can also include receiving an alert notification, where the alert notification is textual or color-based, and where the handheld image capture device displays the alert notification if the temperature is above a maximum temperature threshold or below a minimum temperature threshold.

DETAILED DESCRIPTION

Figure 1:
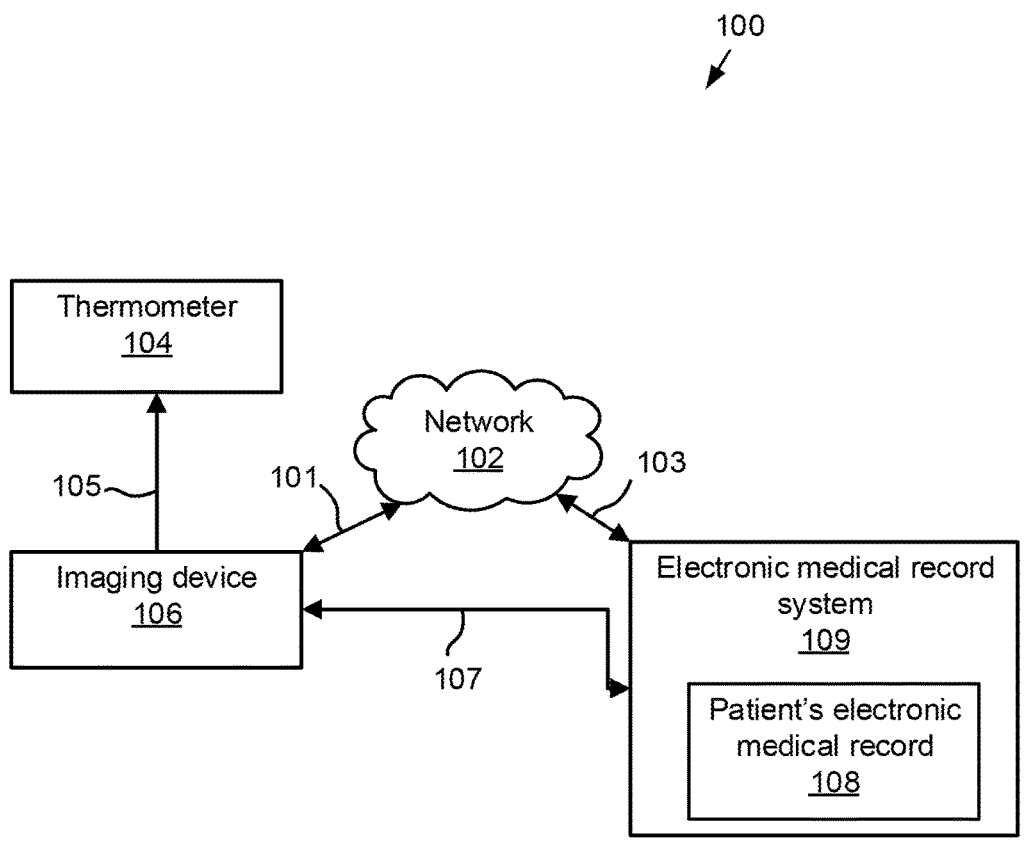
FIG. 1 illustrates one embodiment of an imager and thermometer system including a network, a thermometer, an imaging device, and an electronic medical record.

FIG. 1 is a schematic block diagram illustrating an example system 100 for recording and entering a measured temperature into an electronic medical record. In this example, the system 100 includes a network 102, a medical device, such as a thermometer 104, an imaging device 106, and an electronic medical record 108 of a patient maintained by an electronic medical record system 109. In the example system, the imaging device 106 and the electronic medical record system 109 are in communication either directly via communication path 107 or via the network 102 using wired and/or wireless communication schemes.

Although the examples provided herein are described with respect to a thermometer, the systems and methods are equally applicable to any other medical devices that capture and display vital signs of a patient, such as, for example, a pulse oximeter, an electrocardiograph, blood pressure monitor, etc.

The example thermometer 104 functions to capture a temperature signal, preferably of a patient. The example thermometer is shown in more detail in FIG. 2, which is described further below.

The example imaging device 106 functions to capture 105 the temperature signal of the thermometer 104. In one embodiment, the example imaging device 106 communicates the temperature signal directly via communication path 107 to the electronic medical record 108. In some embodiments, the direct connection via communication path 107 between the imaging device and the electronic medical record system 109 occurs via a universal serial bus (USB) connecting cable in batch mode. In some embodiments, the transfer of information occurs when imaging device 106 is placed in a receiving dock (not pictured), where the receiving dock is in direct communication with the electronic medical record system. Other direct communication configurations are possible.

In one embodiment, the imaging device 106 is connected to the network 102 (connection 101). The network 102 is, in turn, connected to the electronic medical record system 109 (connection 103). The connections 101 and 103 may include any type of wireless network, a wired network, or any communication network known in the art. For example, wireless connections can include cellular network connections and connections made using protocols such as 802.11a, b, and/or g. In other examples, a wireless connection can be accomplished directly between the imaging device 106 and the electronic medical record system 109 using one or more wired or wireless protocols, such as Bluetooth, Wi-Fi Direct, radio-frequency identification (RFID), or Zigbee. Other configurations are possible.

In one embodiment, the imaging device 106 is a dedicated device that is configured to perform the operations described herein. In other embodiments, the imaging device 106 is a mobile device such as a smart phone (e.g., cellular telephone) or a computer tablet, where the mobile device performs the methods and operations described herein while running an application configured to control the operation of the mobile device.

The example electronic medical record system 109 includes the hardware and software required for receiving the communication of the temperature signal from the imaging device 106 and storing the signal in the patient's electronic medical record 108. In some embodiments, the electronic medical record system 109 is configured to transmit an alert to the imaging device 106 after receiving the temperature signal via the direct via communication path 107 or over the network connection 101 and 103. Electronic medical records (EMR) are alternatively known as electronic health records (EHR) or personal health records (PHR), and these three terms can be used interchangeably for the purposes of this document.

The example electronic medical record system 109 includes a processor and memory. In some embodiments, the memory may be stored on a remote device and accessed over a communications network. In some embodiments, the electronic medical record system 109 functions as a central processing unit or server. As described further herein, the electronic medical record system 109 is programmed to store a plurality of medical records so that the records can be created, accessed, and updated.

Figure 5:
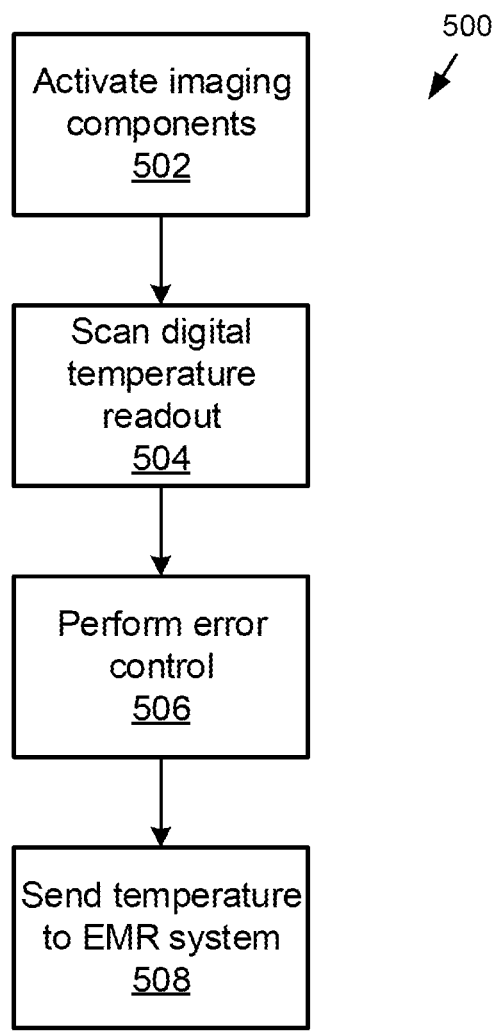
FIG. 5 is a flow chart of an example method of the steps a medical professional performs while operating the hand-held imaging device.
Figure 6:
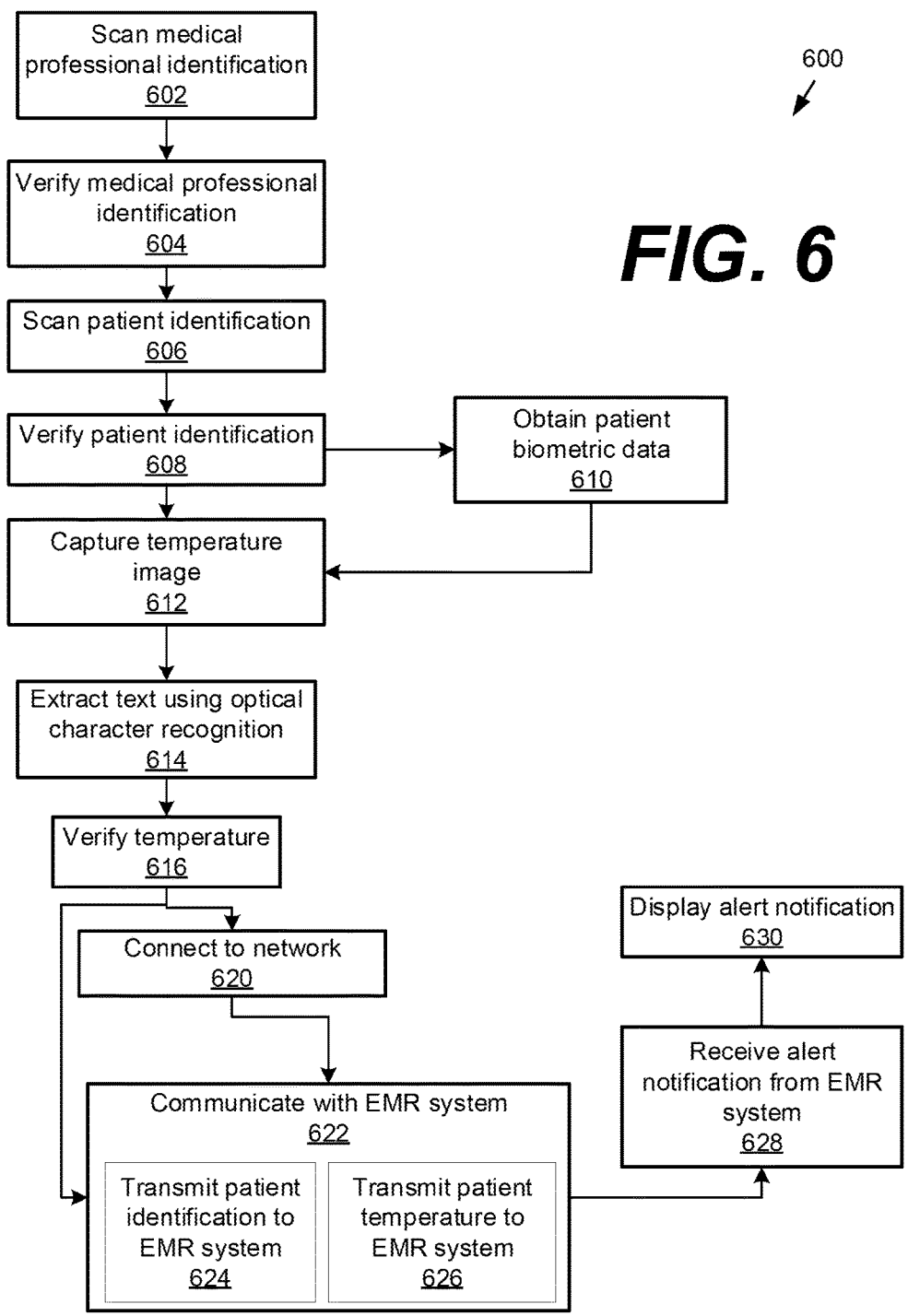
FIG. 6 is a flow chart of an example method of the operation of the hand-held imaging device.

The example electronic medical record 108 is a record corresponding to a specific patient. Example methods of communicating a temperature signal from the imaging device 106 to the electronic medical record system 109 are shown in FIGS. 5 and 6, which are described further below. In some embodiments the electronic medical record 108 contains the vital information of a patient, such as previous measurements of the patient's blood pressure, heart rate, temperature, allergies, medications, previous diagnoses, etc. The electronic medical record 108 can be stored, accessed, and updated using a variety of known techniques.

Figure 2:
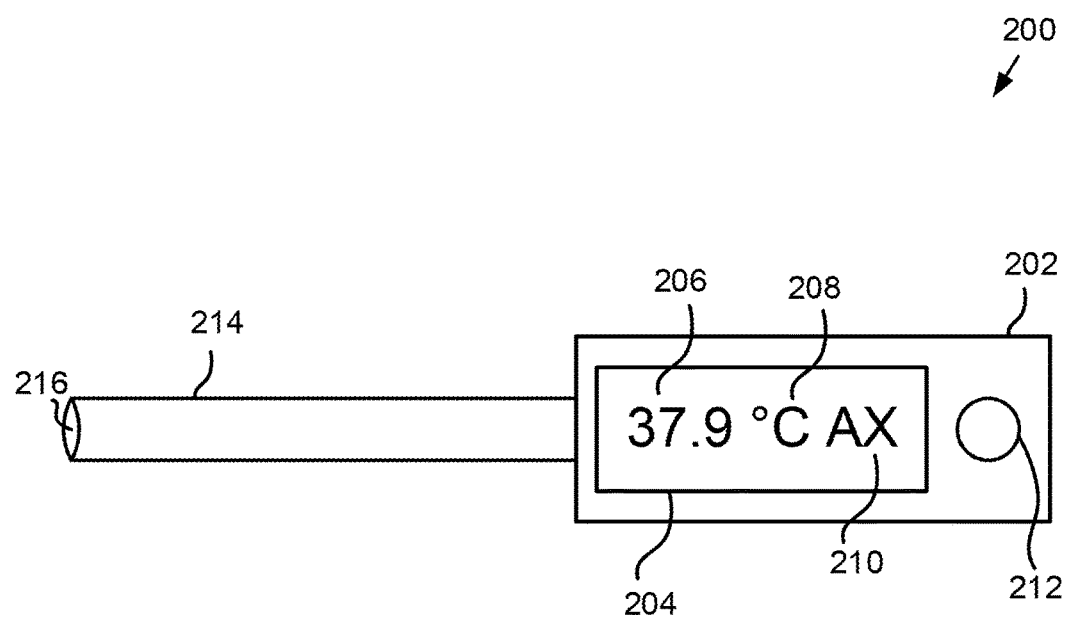
FIG. 2 illustrates one embodiment of a basic digital thermometer sensor.

FIG. 2 illustrates an example of a basic digital thermometer sensor 200. In this example, the thermometer 200 includes a housing 202, a digital display 204, where the display includes a digital temperature reading 206, the temperature unit 208, and one or more error-checking values 210. The housing also includes a button 212 to initiate a temperature measurement. Attached to the housing is an electronic sensor housing 214 that supports an electronic temperature sensor 216. In a preferred embodiment, the thermometer sensor 200 is inexpensively produced.

Thermometer housing 202 supports the display 204, the electronic sensor housing 214, and the button 212 used to initiate a temperature measurement. Additionally, the thermometer housing 202 encloses the components required to, for example, initiate a temperature signal measurement, convert the temperature signal to a digital display 206, generate error-checking values 210, toggle between temperature units 208, monitor battery life, power the digital display 204, and turn off the digital display 204. Additional operations are possible. The components required to perform the operation of the thermometer 200, not pictured in FIG. 2, include, for example, a memory coupled to a processor, which is in turn coupled to the display 204, all of which are powered by a battery that is, for example, rechargeable or a replaceable single use battery.

The thermometer housing 202 is constructed of an inexpensive material, such as, for example, plastic. As depicted in FIG. 2, the thermometer housing 202 is, in some embodiments, shaped as a rectangular prism. Other configurations of the thermometer housing 202 are possible. For example, the thermometer housing 202 is, in some embodiments, shaped like other polyhedra. In other embodiments, the thermometer housing 202 is a continuous shape with the electronic sensor housing 214, such that the two housings, 202 and 214, appear integral to each other.

The digital display 204 includes a digital temperature 206, the units of the temperature 208, and one or more error-checking values 210. The digital display 204 is, in some embodiments, a liquid-crystal display (LCD), an organic light-emitting diode (OLED) display, or an e-ink display. In a preferred embodiment, the digital display 204 is an e-ink display.

The digital temperature 206 is the measurement of the electronic sensor displayed as, in some embodiments, Arabic numerals in sans-serif or serif typeface. The digital temperature 206 is displayed, for example, with accuracy to the ones, tenths, or hundredths place. In a preferred embodiment, the digital temperature 206 is displayed to the tenths place.

The units 208 of the digital temperature 206 are located adjacent to the temperature 206 in the digital display 204. The units 208 include, for example, the degree symbol (°) and an abbreviation of the unit. In most embodiments, the units 208 are either degrees Celsius, displayed as "° C." or degrees Fahrenheit, displayed as "° F.". Conceivably, the thermometer 200 could be configured to display a lesser-used unit, such as Kelvin.

The one or more error-checking values 210 also appear in the example embodiment's display 204. In some embodiments, the error-checking values 210 appear adjacent to the temperature units 208 in the digital display 204. In some embodiments, the error-checking values 210 are one or more characters. In one embodiment, the error-checking values 210 are two characters. The error-checking values 210 can be any type of conventional error-checking values, such as, for example, checksum characters, or characters associated with checksum algorithms such as cyclic redundancy checks (CRC), Fletcher's checksum, or Adler-32. In the embodiments employing error correction algorithms, the checksum characters can be error correction codewords such as Reed Solomon Error Correction codes. In the embodiment where the medical device is an electrocardiograph, the electrocardiogram (ECG) graph can be encoded with a checksum barcode to depict the ECG resolution and image pixel level error correction, or, the entire ECG graph could be encoded in the barcode or 2-dimensional code displayed on the screen.

Button 212 initiates a temperature measurement by the sensor 216. In most embodiments, the button 212 is a physical button supported by the thermometer housing 202. In some embodiments, the button can be a screen button such as a touch screen button. Button 212 is operatively coupled to the temperature sensor 216 so that, in most embodiments, the temperature sensor 216 initiates a temperature measurement protocol when a user depresses the button 212.

The example button 212 in FIG. 2 is circular in shape, but other shapes, such as triangles, rectangles, and squares, are contemplated. Also, additional locations for the button 212 are possible on the housing 202, such as, for example, on the distal end from the sensor, on the surface opposite the display 204, and on the same surface as the display 204 but in a different configuration.

The electronic sensor housing 214 supports the electronic temperature sensor 216. As discussed above, the electronic sensor housing 214 is, in some embodiments, a separate component that is attached to the thermometer housing 202, or, in other embodiments, integral with the thermometer housing 202. In most embodiments, the electronic sensor housing 214 is constructed of plastic or thin metal.

The positional relationship of the electronic temperature sensor 216 and the electronic sensor housing 214 varies by embodiment. In one embodiment, the sensor 216 is located on the distal end of the housing 214. In another embodiment, multiple sensors 216 are located along the exterior of a longitudinal axis of the housings 214. Regardless of configuration, the one or more temperature sensors 216 are operatively connected to the thermometer's processor.

The electronic temperature sensor 216 is disposed in the example embodiment on the end of the sensor housing 214. As mentioned, one or more sensors 216 are employed in alternate embodiments and located at various positions along the housing 214. The electronic temperature sensor 216 is for example, a thermistor, a silicon bandgap temperature sensor, a thermocouple, or a resistance thermometer. Non-contact thermometers can also be used, such as a non-contact infrared thermometer with a display including a checksum.

Figure 3:
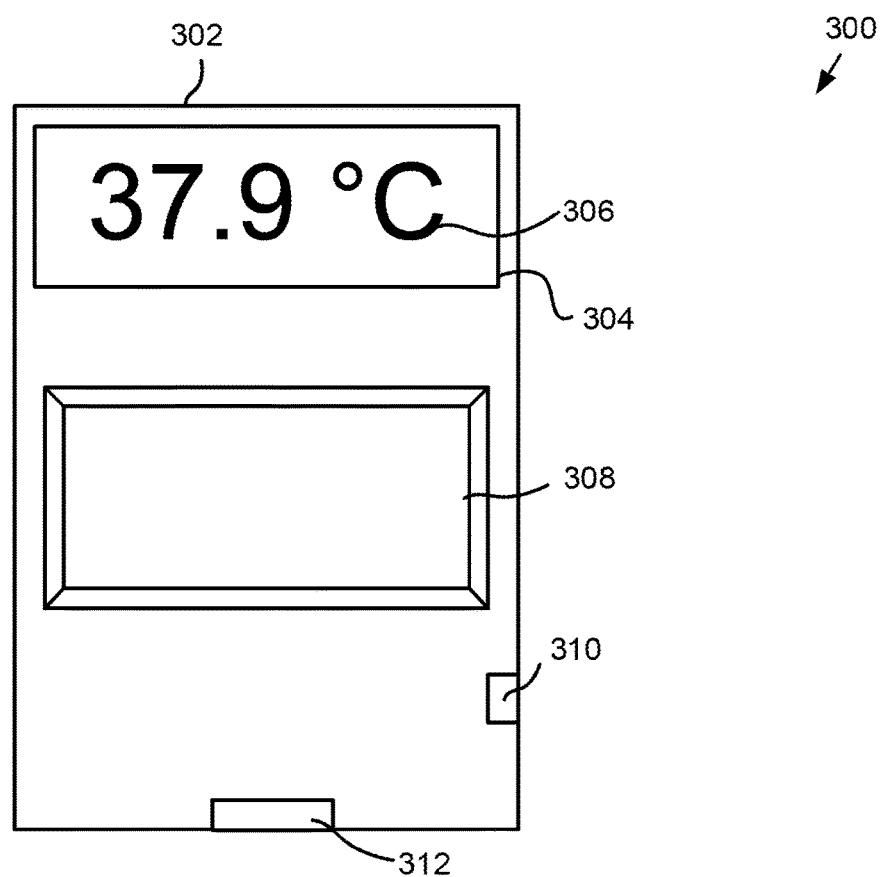
FIG. 3 illustrates a front view of one embodiment of a hand-held imaging device.

FIG. 3 illustrates a front view of an example imaging device 300 for capturing the temperature measured and displayed by the thermometer 200 and transmitting the temperature to the electronic medical record system 109. A rear view of the example imaging device 300 is provided in FIG. 4. In this example, the imaging device 300 includes a housing 302, a display 304 that includes text 306, a button 308, a USB port 310, and a microphone 312. Alternate embodiments can include additional buttons or may not include the USB port 310 or the microphone 312. In other embodiments, the imaging device 300 is a mobile phone or tablet PC.

In this example, the imaging device housing 302 supports the display 304, the button 308, the USB port 310, and the microphone 312. The housing 302 can be constructed of an inexpensive, lightweight material, such as a plastic or a composite material. In most embodiments, the housing is shaped as a rectangular prism with rounded edges. In other embodiments, the housing is more curved, such as, for example, an elliptical prism.

The example housing 302 contains the components necessary for the functions performed by the imaging device 300. In some embodiments, these components, not pictured in FIG. 3, include, for example, a memory, a processor operatively coupled to the memory and the display 304, and a wireless communication unit including components necessary for wireless communication, such as Bluetooth, Zigbee, Wi-Fi, Wi-Fi Direct, and radio-frequency identification (RFID).

In some embodiments, the housing 302 is a key fob. In most embodiments, the housing is sized to be held in one hand, to be light weight, and to fit in a pocket. In some embodiments, the housing also contains components configured to provide tactile and audial feedback, such as vibrations and sounds, respectively.

In the example embodiment 300, the imaging device also has a display 304. The display 304 is, in some embodiments, a liquid-crystal display (LCD) or an organic light-emitting diode (OLED) display. The size and resolution of the display 304 varies in different embodiments, but in all embodiments, the display is capable of displaying text 306. For example, in one embodiment, the display 304 is capable of displaying color and at least four lines of readable text.

In the example embodiment 300, the imaging device also has a button 308. Button 308 is used, in the example embodiment, to initiate an image scan and to interact with instructions or prompts on the screen 304. The size and location of the button vary in different embodiments. Some embodiments have a touch screen that displays a button. In some embodiments, the housing 302 or screen 304 have more than one buttons, used for operations such as, for example, connecting the device to a wireless network, such as Bluetooth or Wi-Fi, or to respond and interact with other on-screen prompts and messages.

In the example embodiment 300, the imaging device also has a USB port 310. The USB port 310 is located on the side of the housing in example embodiment 300, but the port 310 can be positioned in other locations on the housing. In a preferred embodiment, the imaging device 300 has a rechargeable battery that can be recharged through the USB port 310. In some embodiments, the USB port 310 is used to directly connect the imaging device 300 to a dock (not pictured), to the EMR system 109 (not pictured), or any peripheral device (not pictured). USB port 310 may be any size, standard, micro, or mini, or any standard, 1.0, 2.0, or 3.0, for example.

In the example embodiment 300, the imaging device also has a microphone 312. Microphone 312 is an optional component in the imaging device 300. In some embodiments, the imaging device 300 processor is configured to perform voice recognition processing. In those embodiments, the user may state audibly the patient's identification or temperature as an additional error check or in place of scanning the thermometer reading.

Figure 4:
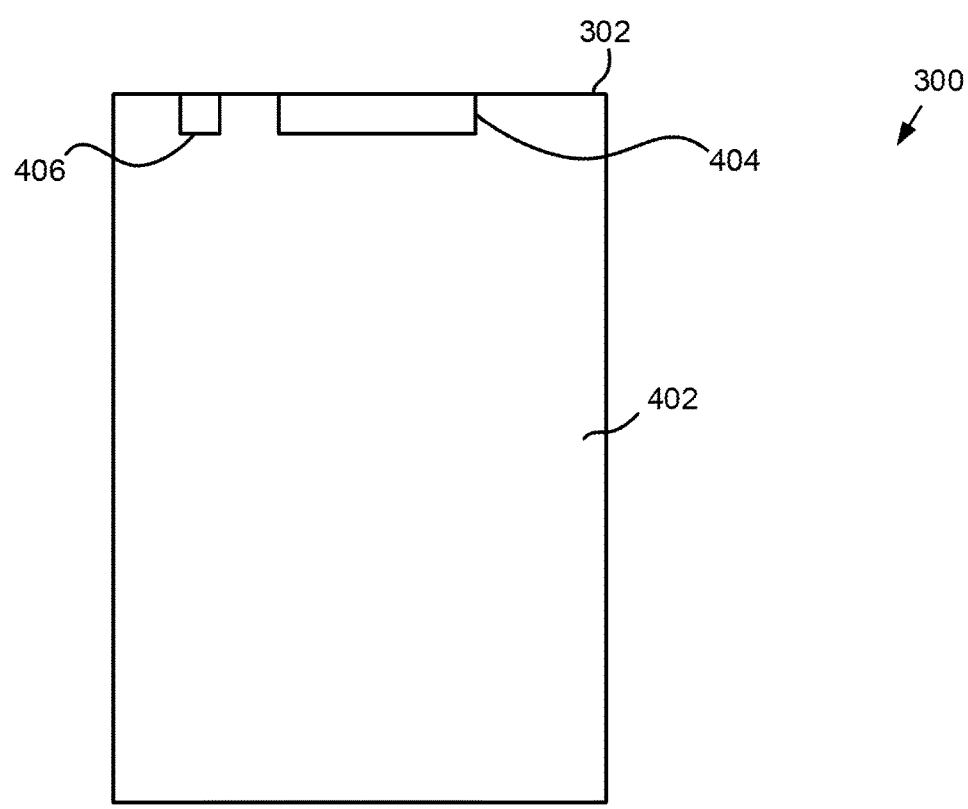
FIG. 4 illustrates a rear view of one embodiment of the hand-held imaging device.

FIG. 4 illustrates a rear view of example imaging device 300. In this example, the imaging device 300 includes a housing 302 with a rear surface 402, as well as an imaging component 404 and a light source 406. In some embodiments, the imaging device 300 is powered by a replaceable battery; the access point for replacing the battery is contemplated to be on the rear surface 402.

As shown in FIG. 4, the imaging component has an operative plane that is parallel to the rear surface of the housing 302. In alternate embodiments, the imaging component 404 operational plane is normal to the rear surface of the housing 302. As discussed above, in some embodiments, the imaging device is a cellular phone or computer tablet. In those embodiments, the imaging device is the camera component in the mobile phone or computer tablet.

In this example, the imaging component 404 includes a camera, including, for example, a lens, a sensor array operatively coupled to the processor and memory in the housing 302. In some embodiments, the camera is configured to automatically focus. Additionally, in this embodiment, the imaging component 404 is operatively coupled to button 308, whereupon the imaging process begins when the user depresses button 308.

In other embodiments, the imaging component 404 includes a visible light-emitting diode, for example, a 650 nm red light-emitting diode or other wavelengths, such as a white light-emitting diode (LED). A lens and a sensor array to receive the reflected LED light, such as, for example, a complementary metal-oxide semiconductor (CMOS), are also provided in these embodiments.

In this example, the imaging component 404 is capable of reading both alphanumeric characters as well as any type of bar code, such as linear bar codes, QR codes, and Microsoft® tags.

In some embodiments, the imaging device 300 includes an illumination source. In some embodiments, the illumination source is at least one light-emitting diode (LED) operatively coupled to the processor, memory, and imaging component 404.

FIG. 5 illustrates a flow chart of an example method 500 of using the imaging device 106. The example method 500 includes activating the imaging components 502, scanning the digital temperature readout 504, performing error control 506, and sending the temperature to the electronic medical record (EMR) system 508.

In this embodiment, the use begins by the user activating the imaging components 502. In a preferred embodiment, the user is a medical professional, such as a nurse, nurse practitioner, physician's assistant, medical student, resident physician, or physician. In many circumstances, the use will occur in a medical facility, such as a clinic or hospital, but none of the methods or uses disclosed herein are limited to being used within a medical facility. At some point in time prior to or concurrent with example method 500, a medical professional will have taken the temperature of the patient. The medical professional taking the temperature of the patient using the thermometer 200 is, in some embodiments, the same professional performing example method 500. In other embodiments, different medical professionals perform the temperature measurement and the example method 500.

Activating the imaging components 502 includes, in some embodiments, the initial setup of the imaging device 106. Initial setup includes, in some embodiments, activating the wireless connectivity of the device 106 to the network 102, activating and syncing the Bluetooth connection with the electronic medical records system 109, and calibrating the imaging component 404. In some embodiments, the imaging device 106 is turned on, or awakened from a sleep or hibernate mode, by pressing button 308. Some embodiments have a dedicated on/off button. Other configurations are possible.

The next step in the example method is for the user to scan the digital temperature readout 504. In one embodiment, the user initiates the scan by pressing button 308 and aiming the imaging component 404 towards the temperature readout. In some embodiments, the user holds down the button 308 until the device captures the temperature image. In other embodiments, the user simply needs to press the button 308 to initiate the temperature image capture.

In this example, the imaging device screen 304 displays the temperature readout if the device 106 was able to read, process, and/or verify the display on the thermometer 206, 208 and 210. In this example, if the imaging device cannot read, process, or verify the thermometer display, the imaging device screen 304 displays a message to the user to retry or rescan the thermometer display, or that there has been an error. Alternatively, or in addition, the imaging device vibrates when the thermometer display is not properly read, although the opposite configuration is also possible—the device vibrates when the display is properly read.

In some embodiments, before or after the user scans the digital temperature 504, the user also scans identifying information. As discussed below with reference to FIG. 6, identifying information includes a medical professional identification, a patient identification number or bar code, for example on a wrist band, or biometric information such as, for example, a fingerprint, a facial geometry, or an eye scan.

After the thermometer display has been scanned, the next step in the example method is for the user to perform error control 506. As discussed above, the thermometer display 204 includes at least one error-checking character 210. The error-checking character or characters is derived from the temperature captured by the thermometer and displayed on the thermometer display.

For example, using known error-checking algorithms such as cyclic redundancy check-16 (CRC-16) or a Reed-Solomon error correction code, the temperature reading is used to generate the error-checking character or characters. The error-checking characters can be imaged at the time the temperature is imaged from the thermometer display. Upon performing character recognition on the temperature and error-checking characters, the temperature and error-checking characters are compared using one of the noted algorithms. If an error is detected, it is assumed that capture and/or character recognition has failed, and an indication for reimaging of the information is provided. Alternatively, in some embodiments, the imaging device continuously reimages until the error-checking algorithms respond correctly, which can be stopped automatically or followed by a signal beep, vibration, or display to stop the reimaging.

The next step in the example method is to send the temperature to the electronic medical record system 508. In some embodiments, this step can occur without the user's initiation. For example, in one embodiment, during the initial setup in step 502, the device 106 is programmed to automatically transmit the captured temperature if the imaging device 106 is directly connected to the EMR system 109 wirelessly, or if the imaging device 106 is connected to the network 102. In other embodiments, the user can initiate the transmission of the temperature to the EMR system 109 by following screen prompts on the imaging device 106 and/or by pressing button 308.

Although the error checking is performed by the imaging devices in this example, other configurations are possible. For example, in a different embodiment, the temperature reading and the error-checking value are both communicated to the electronic medical system. The electronic medical system, in turn, performs the error checking. If an error occurs, the information can be returned to the imaging device in some embodiments.

In a similar manner, the optical character recognition can also be performed by the electronic medical record system in other embodiments. In such a scenario, the image or images are transmitted to the electronic medical records system. The electronic medical records system thereupon performs the optical character recognition and error checking. In yet another example, the image or images can be stored in the electronic medical record.

In an alternate embodiment, the imaging device 106 used to perform the method in FIG. 5 is a cellular telephone or computer tablet. In those embodiments, the mobile phone or tablet (collectively, "mobile device") run an application that is configured to control the imaging component in the mobile device. Additionally, in some embodiments, the application is also configured to scan and interpret the temperature readout 504, perform the error control 506 and send the temperature to the EMR system 508.

FIG. 6 illustrates an example method 600 of the imaging device 106 operations during use by one or more medical professionals. The example method 600 includes scanning one or more medical professionals' identification 602, verifying the medical professional identification 604, scanning a patient identification 606, verifying the patient identification 608, alternatively obtaining patient biometric data 610, capturing the temperature image 612, extracting the text of the temperature image using optical character recognition 614, verifying the temperature 616, connecting to a network 620, communicating with the electronic medical record system 622, transmitting patient identification to the EMR system 624, transmitting the patient's temperature to the EMR system 626, receiving an alert notification from the EMR system 628, and displaying the alert notification 630.

In the example method 600, the user optionally initiates a scan of a professional identification 602, such as, for example, a badge containing a bar code, using the imaging device 106. The scanning operations of the imaging device 106 are described with reference to FIG. 4, above. After scanning the professional identification, the imaging device extracts text using optical character recognition, if necessary, and performs an error check 604 using any error-checking characters present in the professional identification.

In some embodiments, step 602 is necessary to activate the imaging device 106 or the application running on the mobile device. In some embodiments, the professional identification is associated with the patient's temperature reading and sent to the EMR system with the temperature reading. In other embodiments, the imaging device 106 user starts at step 606 or step 612 without first scanning and verifying their own identification. In still other embodiments, the same user uses the same imaging device and the imaging device is configured to store the user's scanned, or otherwise inputted, identification.

In the example method 600, the user optionally initiates a scan of a patient identification 606. The scanning operations of the imaging device 106 are described with reference to FIG. 4, above. After scanning or capturing an image of the patient identification 606, the imaging device 106 performs an error-check using any error checking characters present in the patient identification. In some embodiments, the patient identification is a bar code or bed number associated with the patient. In some embodiments, the imaging device scans patient biometric data 610, either in place of or in addition to the bar code or bed number. In those embodiments, the processor is configured to perform an analysis of the patient's fingerprints, facial geometry, or eyes.

Next, the imaging device 106 captures the temperature image 612 displayed on the thermometer 200. Step 612 is initiated by the imaging device user. In some embodiments, the imaging device 106 emits a guiding light, such as a laser, to help the user aim the device onto the temperature reading. In other embodiments, the imaging device display 304 shows the field of view of the imaging component as a way to guide the user in aiming the device. In the example embodiment, the imaging device 106 is configured to continuously scan until it recognizes at least two numbers corresponding to the patient's temperature and at least one error-checking character.

In some embodiments, the imaging device 106 also tags the image with the current date, time, and/or location data. The location data is obtainable by global positioning systems or network information containing, for example, the closest router, IP address, or any information identifying the specific room or area of the medical facility.

In some embodiments, the imaging device 106 records the type of temperature recorded, such as, for example, oral, under arm, forehead, ear, temporal artery, or rectal. This information can be recorded through, for example, on-screen prompts or by scanning a barcode corresponding to the type of measurement taken. In some embodiments, the imaging device 106 can have the type of measurement taken set as a default and recorded along with the temperature. In some embodiments, the type of temperature information can be displayed in the thermometer display 204 which can be captured by the imaging device 106.

Next, in example method 600, the imaging device 106 extracts the text from the image using an optical character recognition process 614. In most embodiments, the output of step 614 includes a temperature, a unit of temperature measurement, and at least one error-checking character.

In the example method 600, the output of step 614 is used to verify the captured temperature 616. In step 616, the imaging device 106 processor performs the error checking using one or more of the methods described herein.

When the imaging device 106 has verified the temperature extracted from the image text 616, the next step in example method 600 is to either connect to the network 620 or communicate with the EMR system 622 directly. In some embodiments, as discussed above, the imaging device 106 is directly connected to the EMR system 109 via a wireless protocol such as Bluetooth, or through a wired connection, such as a dock or USB connection.

In some embodiments, the imaging device 106 connects to a network 620 through which the device 106 communicates with the EMR system 622. In those embodiments, the EMR system 109 is also connected to the network. Step 622 includes, for example, the exchange of identifying information between the device 106 and system 109, well known to one skilled in the art, as well as steps 624 and 626.

In example method 600, once a communication is established between the imaging device 106 and the EMR system 109, the imaging device 106 transmits the patient identification obtained in steps 606 and/or 610 to the EMR system 109. In some embodiments, the imaging device concurrently or sequentially sends the patient temperature obtained in steps 612, 614 and 616 to the EMR system 109. In some embodiments, the EMR system 109 receives the data from the imaging device 106 and enters the data in the patient's electronic medical record 108.

In example method 600, the imaging device optionally receives an alert from the EMR system 628. In this embodiment, the EMR system 109 compares the patient's temperature to pre-stored parameters and sends an alert if the temperature falls outside those parameters. For example, the parameters are the normal expected temperature for a human, which can vary depending upon the type of measurement taken. The EMR system 109, in some embodiments, sends an alert to the imaging device 106 that the patient's temperature is lower or higher than the expected range.

In some embodiments, the EMR system 109 is configured to compare the instantly transmitted temperature with previous measurements. The EMR system 109, in some embodiments, sends an alert to the imaging device 106 if the temperature is higher than the previous measurement, if the temperature is significantly higher than the previous measurement, such as at least 1-2° F. higher, if the temperature is trending lower, if the temperature is significantly lower than the previous measurement, or if the trend of the previous measurements is increasing or decreasing.

In some embodiments, the EMR system 109 is configured to send custom notifications to the imaging device 106 or is customized to send notifications only at specific temperatures. For example, a physician associated with the patient may be interested in being alerted when the patient's temperature drops below a certain temperature, such as 100° F. In that embodiment, the EMR system 109 is configured to send an alert to the imaging device that a physician should be notified of the patient's current temperature. Other customizations are possible.

In the example method 600, upon receipt of the alert notification, the imaging device 106 displays a message on the screen 630 and/or provides tactile feedback, such as one or more vibrations. For example, in one embodiment the imaging device displays an instruction to the user to retake the patient's temperature or set an alarm to retake the patient's temperature in the future. The image device 106 is configured, in some embodiments, to store and display pre-determined notifications or to display other notifications received from the EMR system 109, such as "Notify Physician".

Figure 7:
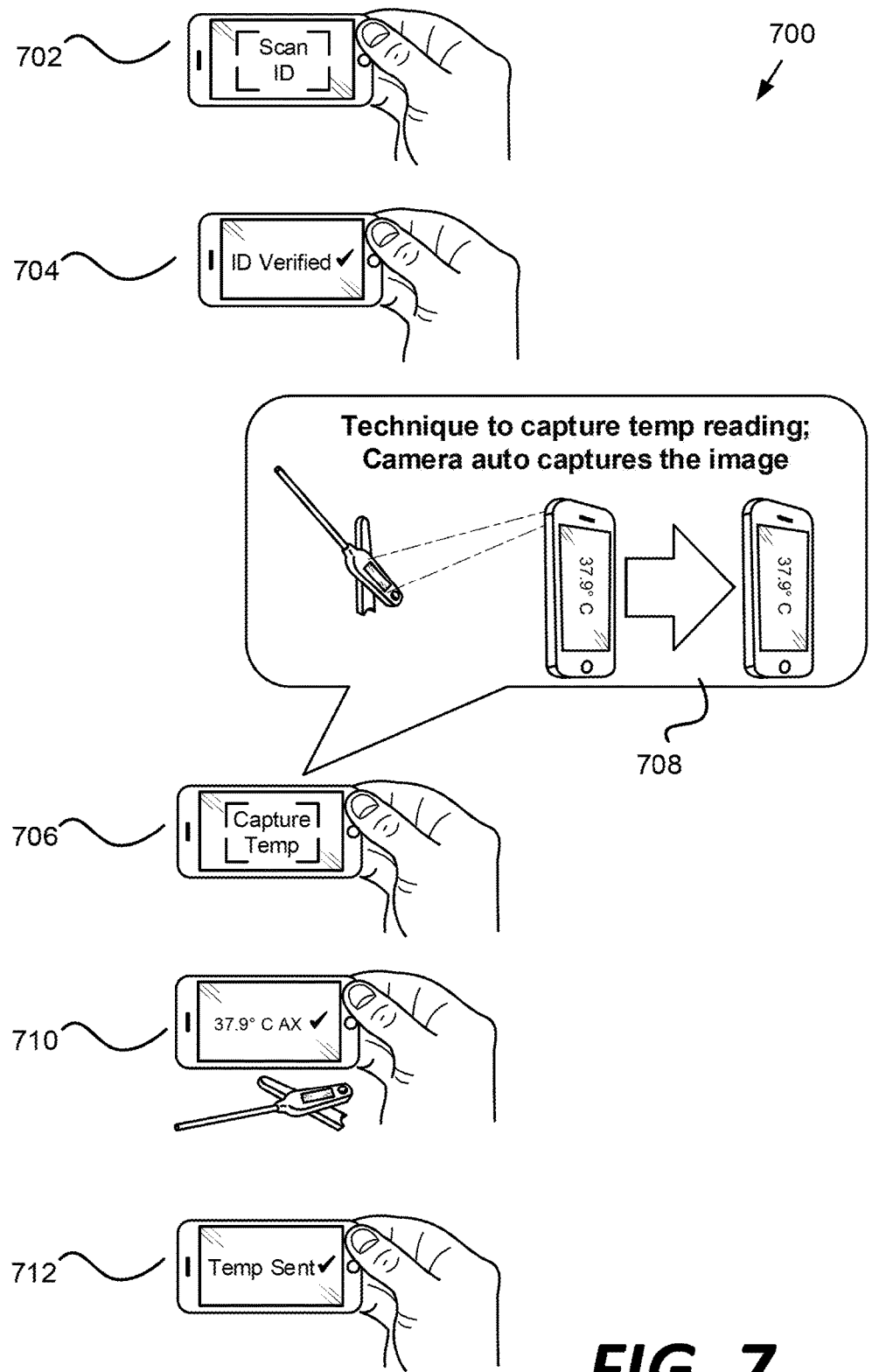
FIG. 7 is an example graphical user interface illustrating multiple displays during the operation of the hand-held imaging device.

FIG. 7 illustrates a set 700 of example graphical user interfaces at various points in the example method shown in FIG. 6. The example set 700 includes an identity scan screen 702, a confirmation of identity verification screen 704, a capture temperature screen 706, a call-out showing the capture temperature screens 708, a temperature verification screen 710, and a temperature sent screen 712. In the embodiment shown, the imaging device is a smart phone including a display, a camera, and wireless connectivity functionality, running an application configured to implement example method 600.

In the example 700, identity scan screen 702 appears for scanning the medical professional identification 602 and for scanning the patient identification 606. The screen display includes guide lines to help the user frame the identification in the display, which in turn, enables the camera to capture the identification and use the image for further processing. Other embodiments for guiding the user are possible, such as, for example, using a blackout frame. Also included in the example display are the instructions "Scan ID". In other embodiments, the position of the words is different and/or omitted. Other words directing the user are possible.

Example graphical user interfaces 700 also include identity confirmation screen 704 informing the user that, in some embodiments, the imaging device successfully scanned the identification and converted the image to readable text. In other embodiments, confirmation screen 704 varies in design and/or content. In some embodiments, confirmation screen 704 appears on the device accompanied by tactile or audial feedback, such as a vibration or a beep, respectively. In some embodiments, the confirmation screen 704 is displayed when the imaging device 106 communicates with the EMR system 109 and verifies that the identification scanned, for example, the patient or professional identification, has a corresponding entry in the system 109 database.

Example graphical user interfaces 700 also include capture temperature screen 706. Similar to scan identity screen 702, the imaging device screen in this example contains demarcations to guide the user in aiming the imaging component towards the temperature reading. Callout 708 depicts graphically two of the operations, in this embodiment, the imaging device performs when the user aims the device on the temperature reading: scanning the thermometer readout and converting the image to text.

Example graphical user interfaces 700 also include temperature verification screen 710. In this example, the imaging device screen provides notification that the device was able to read the thermometer text and that the error-correction processes confirmed that the scanned temperature is correct. In some embodiments, temperature verification screen 710 displays the temperature, the units of measurement, and the error-checking value or values.

Example graphical user interfaces 700 also include temperature sent screen 712. In other embodiments, temperature sent screen 712 varies in design and/or content. In some embodiments, temperature sent screen 712 appears on the device accompanied by tactile or audial feedback, such as a vibration or a beep, respectively. In this example, the confirmation screen 712 appears on the imaging device screen when the imaging device has successfully connected to the EMR system directly or through the network, and successfully transmitted the temperature and any additional data associated with the temperature to the EMR system.

The flow diagrams depicted herein are just examples. There may be many variations to these diagrams or the steps (or operations) described therein without departing from the spirit of the disclosure. For instance, the steps may be performed in a differing order, or steps may be added, deleted or modified.

While embodiments have been described, it will be understood that those skilled in the art, both now and in the future, may make various improvements and enhancements can be made.

What is claimed is:

1. A handheld imaging device, comprising:
   a housing;
   a camera supported by the housing and configured to capture a visual image containing text displayed by a thermometer, the text displayed by the thermometer including both a value representing a physiological measurement and a checksum value;
   a processor operatively coupled to the camera and configured to:
      extract the text from the visual image using optical character recognition, and
      compare the value representing the physiological measurement and the checksum value to check for errors in the optical character recognition of the image;
   a display on the housing configured to display the text; and
   a network connection unit operatively coupled to the processor,
   wherein the network connection unit is configured to communicate with an electronic medical record system and to transmit at least some of the extracted text to the electronic medical record system, and
   wherein the processor is further configured to provide at least one of a message to capture a new visual image or an error message on the display screen, if the imaging device is not able to read, process or verify the value representing the physiological measurement.

2. The handheld imaging device of claim 1, wherein the error-control includes using an error detection function to verify an integrity of the value representing the physiological measurement.

3. The handheld imaging device of claim 1, wherein the error-control includes using an error correction function to correct error of the value representing the physiological measurement.

4. The handheld imaging device of claim 1, wherein the camera is configured to image a temperature reading provided by a thermometer.

5. The handheld imaging device of claim 1, further comprising:
   a code interpretation module configured to interpret any one of the following in the image: a barcode or a quick response code.

6. The handheld imaging device of claim 1, wherein the network connection unit communicates with the electronic medical system wirelessly.

7. The handheld imaging device of claim 1, wherein the housing is a key fob.

* * * * *